United States Patent
Bell et al.

(10) Patent No.: US 7,326,735 B2
(45) Date of Patent: Feb. 5, 2008

(54) FORMULATIONS FOR ANAESTHETIC USE

(75) Inventors: Alan R. Bell, Woollahra (AU); Fenella Cochrane, Frencs Forest (AU); Geoffrey N. O'Connor, Loftus (AU); James S. Rowe, Kogarah (AU)

(73) Assignee: Parnell Laboratories (Aust) Pty Limited, New South Wales (AU)

( * ) Notice: Subject to any disclaimer, the term of this patent is extended or adjusted under 35 U.S.C. 154(b) by 247 days.

(21) Appl. No.: 10/833,429

(22) Filed: Apr. 28, 2004
(Under 37 CFR 1.47)

(65) Prior Publication Data
US 2005/0004234 A1 Jan. 6, 2005

Related U.S. Application Data

(60) Provisional application No. 60/466,951, filed on Apr. 30, 2003.

(30) Foreign Application Priority Data

Jun. 9, 2003 (NZ) ................. 526347
Jun. 10, 2003 (AU) ............. 2003204596

(51) Int. Cl.
A01N 31/08 (2006.01)
A61K 31/05 (2006.01)
(52) U.S. Cl. ................. 514/730; 514/731
(58) Field of Classification Search ........ 514/730, 514/731
See application file for complete search history.

(56) References Cited

U.S. PATENT DOCUMENTS 6,140,373 A 10/2000 May et al. ............ 514/731
6,743,436 B1 * 6/2004 Lee et al. ............. 424/423
2001/0004644 A1 * 6/2001 Levin ................. 514/646
2004/0067919 A1 4/2004 Jee ................... 514/171

FOREIGN PATENT DOCUMENTS

KR 10 2004 0031962 A 4/2004
WO WO 2004/032910 A 4/2004

OTHER PUBLICATIONS

Macht et al, Pharmacological and therapeutic study of benzyl alcohol as a local anesthetic, J. Pharmacol., 1918, 12, 263-79.*
Examination report in counterpart New Zealand application No. 526347 dated May 17, 2005.

* cited by examiner

*Primary Examiner*—Alton Pryor
(74) *Attorney, Agent, or Firm*—Marshall, Gerstein & Borun LLP

(57) ABSTRACT

A formulation for anaesthetic use is described. The formulation contains propofol, and may be used to induce and/or maintain anaesthesia or sedation in a vertebrae. The formulation additionally contains a solvent or a combination of solvents and is suitable for mixing with commonly used infusion fluids prior to injection in to a patient. The formulation may be terminally sterilised using moist heat in order to assure sterility, and contains no lipid, thereby avoiding complications associated with administration over prolonged periods of time, or to patients with disorders of fat metabolism.

33 Claims, No Drawings

FORMULATIONS FOR ANAESTHETIC USE

CROSS-REFERENCE TO RELATED APPLICATION

The benefit of the Apr. 30, 2003 filing date of U.S. Provisional patent application Ser. No. 60/466,951 is hereby claimed under 35 U.S.C. 119(e).

The present invention relates to formulations for anaesthetic use containing propofol.

BACKGROUND ART

Propofol is an anaesthetic that can be used to induce and maintain general anaesthesia and for sedation. Propofol is used as an anaesthetic in both medical and veterinary applications. Injectable anaesthetics such as propofol must be administered directly into the blood stream. Propofol is a rapidly acting intravenous agent that produces anaesthesia of snort duration without excitatory side effects. Recovery from anaesthesia is smooth and rapid, and is unaffected by prolonged or repeat administration.

Water is generally the solvent of choice for parenteral formulations. Anaesthetic agents are generally lipid soluble molecules, as the drug must possess sufficient lipid solubility to cross the blood-brain barrier and exert its action. However, highly lipid soluble molecules are generally poorly soluble in water and thus are difficult to formulate for intravenous injection. Propofol is a hydrophobic water-insoluble oil. Although for some anaesthetics it may be possible to obtain a water-soluble salt of the anaesthetic agent that releases a lipid soluble free base in vivo, to date this has not proved feasible for propofol and no such compound is commercially available.

To develop an aqueous formulation of propofol, non-aqueous solubilising aids, eg organic solvents, must be used in order to obtain a stable, convenient parenteral dosage form. The chosen solubilising aid should have minimal toxic, irritating and sensitising potential. The solubilising aids should have no or minimal inherent pharmacological activity themselves, and should not adversely affect the pharmacological activity of the propofol.

Various solvents have been used previously. However, whilst use of a single solvent may be adequate to solubilise the propofol, generally the solvent must be present in high concentrations, with attendant toxic potential. Such formulations also have the disadvantage that, upon subsequent dilution with many commonly used pharmaceutical intravenous fluids, the propofol will precipitate out of solution as the drug's solubility in the solvent system is exceeded.

Propofol has been solubilised with Cremophor EL (polyethylene glycol triricinoleate 35) and presented in aqueous formulation (U.S. Pat. No. 4,452,817; U.S. Pat. No. 4,056,635). However, such formulations present a risk of anaphylactoid reactions and demonstrate a high incidence of pain on injection.

Emulsions of propofol have also been utilised. The majority of such formulations utilise some form of oil-in-water emulsion or encapsulation of propofol in order to deliver the anaesthetic agent to the patient.

Commercially available propofol formulations are all oil-in-water emulsions comprising 1% propofol in soya bean oil, egg phosphatide and glycerol. Disadvantages of the commercially available formulations of propofol are that they have potential for elevating serum triglycerides when administered to patients with impaired fat metabolism and/or for extended periods of time due to the high lipid content of the formulation. Furthermore, dilution of such formulations prior to administration is restricted due to the nature of the emulsion. Moreover, such formulations present a risk of bacterial contamination with rapid growth of bacteria due to the lack of antimicrobial preservatives and high nutritive value of the formulation. Any broached container must be used within a short period of time or discarded due to the risk of microbial contamination and growth. Further, such formulations are not suitable for terminal sterilisation by moist heat given the heat-sensitive nature of the excipients.

None of the known formulations are suitable for infinite dilution with water or commonly used infusion fluids.

Clinically, it would be advantageous to formulate an injectable propofol formulation that is a homogenous solution of the drug in an aqueous based pharmaceutically acceptable solvent system free from fat, which can be administered by intravenous bolus injection, and which can be diluted infinitely with commonly used fluids. In addition, the formulation should not present a risk of anaphylactoid reactions in susceptible individuals, as is the case with Cremophor-based formulations.

SUMMARY OF THE INVENTION

In this specification and claims, a solvent is taken to be a usually liquid substance capable of dissolving or dispersing one or more other substances, solubilising is taken to be the process of said dissolving or dispersing, and a solution is taken to be the product of said dissolving or dispersing. The solvent may be a surfactant and/or an emulsifying agent or other suitable solvent for propofol, either by itself (such as in the first aspect, described below for example) or in combination with at least one other solvent (such as in the second to fifth aspects, described below for example). The second aspect includes a solvent together with water (which is also a solvent) and the fourth and fifth aspects include two solvents together with water.

Also, in this specification, all ratios, proportions and percentages of components may be expressed as w/w, w/v, v/w or v/v unless otherwise specified.

According to a first aspect of the present invention there is provided a formulation for anaesthetic use, comprising:
propofol, and
a solvent,
wherein said solvent is clinically acceptable and wherein the formulation does not contain a condensation product of ethylene oxide with a fatty acid (for example lauric acid, stearic acid or oleic acid), or with a vegetable oil (for example castor oil or a derivative of castor oil), or with a long chain aliphatic alcohol (for example cetyl alcohol, lauryl alcohol, stearyl alcohol or oleyl alcohol), or with a partial ester derived from a fatty acid and a hexitol anhydride, or with propylene oxide. Examples of the above materials which are excluded from this aspect of the invention are Myrj 52, Myrj 53, Cremophor EL, Cremophor RH40, Brij 35, Emulphor EL 620, Texophor D40, Tween 40, Tween 60, Tween 80 and Pluronic F68. The solvent may be a polyglycol ester of polyethylene glycol and 12-hydroxystearic acid. The ratio of propofol to the solvent is such that the propofol is solubilised in the solvent. Said ratio may be between 1:199 and 1:6, or between 1:99 and 1:6, or between 1:60 and 1:6, or between 1:30 and 1:8, or between 1:20 and 1:9, or may be about 1:10. The formulation of the first aspect may be capable of infinite dilution with water without phase separation.

In an embodiment, the ratio of propofol to the solvent is such that the clarity of the formulation is selected from the group consisting of clear, substantially clear, translucent, slightly cloudy, and slightly hazy.

In another embodiment there is provided a formulation for anaesthetic use, comprising:
propofol, and
a solvent, wherein said solvent is selected from the group consisting of glycofurol, Solutol HS15, a polyglycol ester of polyethylene glycol and 12-hydroxystearic acid, and mixtures thereof. Glycofurol (also known as glycofuranol or tetraglycol) is α-(tetrahydro-2-furanyl)methyl-ω-hydroxy-poly(oxy-1,2-ethanediyl). Solutol HS15 (polyethylene glycol 660 12-hydroxy stearate) is available from BASF Ludvigshafen, Germany. Solutol HS15 is a trademark. The nature of the solvent used in the formulation of the first aspect is such that the risk of causing anaphylactoid reactions in susceptible individuals is less than that of Cremophor EL. This risk may be low or negligible.

In a further embodiment there is provided a formulation for anaesthetic use, comprising:
propofol, and
a solvent, wherein the solvent is selected from the group consisting of glycofurol, Solutol HS15 (polyethylene glycol 660 hydroxy stearate), a polyglycol ester of polyethylene glycol and 12-hydroxystearic acid, and mixtures thereof, and wherein the ratio of propofol to the solvent is such that the propofol is solubilised.

According to a second aspect of the present invention there is provided an aqueous formulation for anaesthetic use, comprising:
propofol,
a solvent, and
water, wherein said solvent is clinically acceptable and wherein the formulation does not contain a condensation product of ethylene oxide with a fatty acid, or with a vegetable oil, or with a long chain aliphatic alcohol, or with a partial ester derived from a fatty acid and a hexitol anhydride, or with propylene oxide. The amount of solvent and water in the formulation is such that the propofol is solubilised therein. The formulation of the second aspect may be capable of infinite dilution in water without phase separation.

In an embodiment, the ratio of the solvent to water is such that the clarity of the formulation is selected from the group consisting of clear, substantially clear, translucent, slightly cloudy, and slightly hazy. This may be between 1:40 and 1:2, or between 1:40 and 1:4, or may be between 1:25 and 1:5, or may be between 1:10 and 3.10, and may be about 1:5.

The formulation may additionally contain other components such as are desirable in the formulation, for example antimicrobial agents. A suitable antimicrobial agent may be benzyl alcohol or methyl paraben or another suitable compound. The nature of the solvent used in the formulation of the second aspect is such that the risk of causing anaphylactoid reactions in susceptible individuals is less than that of Cremophor EL. The risk may be low or negligible. The solvent may be a polyglycol ester of polyethylene glycol and 12-hydroxystearic acid.

In another embodiment there is provided a formulation for anaesthetic use, comprising:
propofol,
a solvent, and
water, wherein said solvent is selected from the group consisting of glycofurol, Solutol HS15, a polyglycol ester of polyethylene glycol and 12-hydroxystearic acid, and mixtures thereof.

In a further embodiment there is provided a formulation for anaesthetic use, comprising:
propofol,
a solvent, and
water, wherein the solvent is selected from the group consisting of glycofurol, Solutol HS15 (polyethylene glycol 660 hydroxy stearate), a polyglycol ester of polyethylene glycol and 12-hydroxystearic acid, and mixtures thereof, and wherein the amounts of solvent and water in the formulation is such that the propofol is solubilised.

According to a third aspect of the present invention there is provided a formulation for anaesthetic use, comprising:
propofol,
a first solvent, and
a second solvent which is different to said first solvent, wherein said solvents are clinically acceptable, the first solvent is not a condensation product of ethylene oxide with a fatty acid, or with a vegetable oil, or with a long chain aliphatic alcohol, or with a partial ester derived from a fatty acid and a hexitol anhydride, or with propylene oxide, and the second solvent is not ethanol or a glycol or a polyethylene glycol or a glycol monoether or a water soluble ester or amide. The second solvent may be a polyglycol ester of polyethylene glycol and 12-hydroxystearic acid. The amounts of the first and second solvents in the formulation are such that the propofol is solubilised.

In an embodiment, the ratio of the first solvent to the second solvent may be such that the clarity of the formulation is selected from the group consisting of clear, substantially clear, translucent, slightly cloudy, and slightly hazy, and may be between 6:1 and 0.6:1, or between 4:1 and 1:1, or between 3:1 and 1:1, or may be about 2:1.

The formulation of the third aspect may be capable of infinite dilution in water without phase separation.

In another embodiment there is provided a formulation for anaesthetic use, comprising:
propofol,
a first solvent, and
a second solvent which is different to said first solvent, wherein the first solvent is selected from the group consisting of glycofurol, Macrogol 400 (polyethylene glycol 400), polyethylene glycol (PEG), propylene glycol and mixtures thereof and the second solvent is Solutol HS15, a polyglycol ester of polyethylene glycol and 12-hydroxystearic acid, or a mixture thereof, or the first solvent is glycofurol and the second solvent is selected from the group consisting of all esters of long-chain polyethylene glycol with structures containing no less than 10 carbon atoms.

In a further embodiment there is provided a formulation for anaesthetic use, comprising:
propofol,
a first solvent, and
a second solvent which is different to said first solvent, wherein the first solvent is selected from the group consisting of glycofurol, Macrogol 400 (polyethylene glycol 400), polyethylene glycol (PEG), propylene glycol and mixtures thereof and the second solvent is selected from the group consisting of Solutol HS15 (polyethylene glycol 660 hydroxy stearate), a polyglycol ester of polyethylene glycol and 12-hydroxystearic acid, and mixtures thereof, and wherein the amounts of the first and second solvents in the formulation are such that the propofol is solubilised.

According to a fourth aspect of the present invention there is provided a formulation for anaesthetic use comprising:
propofol,
a first solvent,
a second solvent which is different from said first solvent, and
water,
wherein said solvents are clinically acceptable, the first solvent is not a condensation product of ethylene oxide with a fatty acid, or with a vegetable oil, or with a long chain aliphatic alcohol, or with a partial ester derived from a fatty acid and a hexitol anhydride, or with propylene oxide, and the second solvent is not ethanol or a glycol or a polyethylene glycol or a glycol monoether or a water soluble ester or amide. The ratios of propofol, the first solvent, the second solvent and water may be such that the propofol is solubilised.

In an embodiment, the ratios of propofol, the first solvent, the second solvent and water may be such that the clarity of the formulation is selected from the group consisting of clear, substantially clear, translucent, slightly cloudy, and slightly hazy.

The second solvent may be a polyglycol ester of polyethylene glycol and 12-hydroxystearic acid. The formulation of the fourth aspect may be capable of infinite dilution in water without phase separation.

In another embodiment there is provided a formulation for anaesthetic use, comprising:
propofol,
a first solvent,
a second solvent which is different from said first solvent, and
water,
wherein the first solvent is selected from the group consisting of glycofurol, Macrogol 400, polyethylene glycol (PEG), propylene glycol and mixtures thereof and the second solvent is Solutol HS15, a polyglycol ester of polyethylene glycol and 12-hydroxystearic acid, or a mixture thereof, or the first solvent is glycofurol and the second solvent is selected from the group consisting of all esters of long-chain polyethylene glycol with structures containing no less than 10 carbon atoms.

In a further embodiment there is provided a formulation for anaesthetic use comprising:
propofol,
a first solvent,
a second solvent which is different from said first solvent, and
water,
wherein the first solvent is selected from the group consisting of glycofurol, Macrogol 400 (polyethylene glycol 400), polyethylene glycol (PEG), propylene glycol and mixtures thereof and the second solvent is Solutol HS15 (polyethylene glycol 660 hydroxy stearate), a polyglycol ester of polyethylene glycol and 12-hydroxystearic acid, or a mixture thereof and wherein the amounts of propofol, the first and second solvents and water in the formulation are such that the propofol is solubilised.

According to a fifth aspect of the invention there is provided a formulation for anaesthetic use comprising:
propofol in a range of about 0.5% to about 1.5%;
a first solvent in a range of about 10% to about 30%;
a second solvent which is different from said first solvent in a range of about 5% to about 15%; and
water to 100%,
wherein said solvents are clinically acceptable, the first solvent is not a condensation product of ethylene oxide with a fatty acid, or with a vegetable oil, or with a long chain aliphatic alcohol, or with a partial ester derived from a fatty acid and a hexitol anhydride, or with propylene oxide, and the second solvent is not ethanol or a glycol or a polyethylene glycol or a glycol monoether or a water soluble ester or amide. The second solvent may be a polyglycol ester of polyethylene glycol and 12-hydroxystearic acid. The formulation may be capable of infinite dilution with water without phase separation.

The anaesthetic formulation may include one or more clinically acceptable auxiliary agents in a total amount of up to 15%, 12%, 10%, 8%, 6%, 5%, 4%, 3%, 2% or 1%, for example. The anaesthetic formulation may include one or more clinically acceptable auxiliary agents in the range of 0.1%-15%, 0.5%-10%, 0.5-5%, or 1%-5%, for example. Alternatively, the anaesthetic formulation may not include one or more clinically acceptable auxiliary agents.

The water may be sterile water, water for injections, or other suitable water. The formulation of the invention may be diluted prior to use. Suitable diluents may be selected from Ringers Solution, Hartmanns Solution, Dextrose Solution, Saline Solution and Sterile Water for Injection, for example.

In an embodiment there is provided a formulation for anaesthetic use, comprising:
propofol in a range of about 0.5% to about 1.5%;
a first solvent in a range of about 10% to about 30%;
a second solvent which is different from said first solvent in a range of about 5% to about 15%; and
water to 100%,
wherein the first solvent is selected from the group consisting of glycofurol, Macrogol 400, polyethylene glycol (PEG), propylene glycol and mixtures thereof and the second solvent is Solutol HS15, or the first solvent is glycofurol and the second solvent is selected from the group consisting of all esters of long-chain polyethylene glycol with structures containing no less than 10 carbon atoms. The second solvent may be a polyglycol ester of polyethylene glycol and 12-hydroxystearic acid.

In another embodiment there is provided a clinically acceptable formulation for anaesthetic use, comprising:
propofol in a range of about 0.5% to about 1.5%;
a first solvent in a range of about 10% to about 30%;
a second solvent which is different from said first solvent in a range of about 5% to about 15%; and
water to 100%,
wherein the formulation contains no fats, the first solvent is glycofurol and the second solvent is Solutol HS15 and the concentrations of glycofurol and Solutol HS15 in the formulation are such that the risk of causing anaphylactoid reactions in susceptible individuals is low or negligible.

With reference to the first, second, third, fourth or fifth aspect of the invention, the formulation may include one or more of a viscosity-modifying agent, an antimicrobial preservative and an antioxidant.

The concentration of propofol in the formulation of the invention may be in a range of about 0.5% to about 17%, for example about 0.5% to about 5%, about 0.75% to about 4%, about 0.8% to about 3%, about 0.85% to about 2.5%, about 0.9% to about 2.0%, about 0.95% to about 1.75%, about 1% to about 1.5%, about 0.5% to about 1.5%, about 0.9% to about 1.2%, or about 1% to about 1.1%. Preferably the concentration of propofol in the formulation of the invention may be about 1%.

The concentration of the first solvent in the formulation of the third, fourth or fifth aspect of the invention may be in a range of about 5% to about 40%, for example about 10 to about 30%, about 15% to about 25%, about 16 to about 24%, about 18 to about 22%, or about 19 to about 21%. The concentration of first solvent in the formulation may be about 20%. The nature of the first solvent and/or concentration of the first solvent in the formulation are such that the risk of causing anaphylactoid reactions in susceptible individuals is less than that of Cremophor EL. The risk may be low or negligible.

The concentration of the second solvent in the formulation of the third, fourth or fifth aspect of the invention may be in a range of about 1 to about 20%, about 5 to about 15%, about 7.5% to about 12.5%, about 8% to about 12%, about 9% to about 11%, or about 9.5% to about 10.5%. The second solvent may be present in an amount of about 10%. The nature of the second solvent and/or concentration of the second solvent in the formulation are such that the risk of causing anaphylactoid reactions in susceptible individuals is less than that of Cremophor EL. The risk may be low or negligible.

The total volume of the formulation of the invention may be made up to 100% with water.

The ratio of the first solvent to the second solvent in the third, fourth of fifth aspect of the formulation may be about 20:1 to about 1:20, or may be about 5:1 to about 1:1.5. For example, the ratio of the first solvent to the second solvent may be about 5:1, about 4:1, about 3:1, about 2.5:1, about 2.25.1, about 2:1, about 0.75:1, about 1.5:1, about 1:1, about 1:1, or about 1:1.25. For instance, the ratio of the first solvent to the second solvent may be about 2.5:1, 2:1 or 1:1.

The formulation of the invention may optionally include a pharmaceutically acceptable viscosity-modifying agent. Suitable viscosity-modifying agents include lower alkyl alcohols, such as ethanol, for example Ethanol BP. The concentration of the viscosity-modifying agent in the formulation of the invention may be in a range of about 1.8% to about 2.2%, for example about 1.9% to about 2.1%. The viscosity-modifying agent may be present in an amount of about 2%.

The formulation of the invention may additionally include at least one antimicrobial agent selected from the group including, but not limited to, benzalkonium chloride, benzethonium chloride, benzyl alcohol, benzoic acid, chlorobutanol, chlorocresol, cresol, methyl paraben, propyl paraben, sodium benzoate, or a combination of 2 or more of those listed. Preferably, the antimicrobial agent is benzyl alcohol. When present, the concentration of antimicrobial agent in the formulation may be in a range of about 0.01% to about 2.2%, for example, about 0.02% to about 2.0%, about 0.05% to about 1.8%, 0.1% to about 1.6%, about 0.5% to about 1.5%, about 0.75% to about 1.4%, about 1% to about 1.2%.

The formulations of the invention are free from fats.

Optionally, the formulation of the invention may additionally include at least one antioxidant selected from the group including, but not limited to, butylated hydroxyanisole, propyl gallate and butylated hydroxytoluene. When present, the concentration of the antioxidant in the formulation may be in a range of about 0.002% to 0.02%.

The solvents used in the formulation of the invention are clinically acceptable solvents. The solvents are used in the formulations of the invention in clinically acceptable amounts. One of the advantages of the multi solvent formulations of the invention is that where one of the solvents would be toxic to a host if it were to be used in too high amount in the formulation, a less than toxic amount of that solvent can be used in the formulation and another solvent can be used (which may be water or as well as water in certain of the formulations of the invention) in a less than toxic amount to provide a formulation that has a low risk of causing a toxic reaction in the user.

According to a sixth aspect of the invention, there is provided a process for preparing a formulation for anaesthetic use, comprising the step of dissolving propofol in a solvent, wherein said solvent is clinically acceptable and wherein the formulation does not contain a condensation product of ethylene oxide with a fatty acid, or with a vegetable oil, or with a long chain aliphatic alcohol, or with a partial ester derived from a fatty acid and a hexitol anhydride, or with propylene oxide, and wherein the ratio of propofol to the solvent is such that the propofol is solubilised in the solvent. Said ratio may be between 1:199 and 1:6, or between 1:99 and 1:6, or between 1:60 and 1:6, or between 1:30 and 1:8, or between 1:20 and 1:9, or may be about 1:10. The solvent may be a polyglycol ester of polyethylene glycol and 12-hydroxystearic acid. Said dissolving may include one or more of the steps of:

shaking and or stirring;

allowing propofol and the solvent to stand.

In an embodiment, the ratio of propofol to the solvent is such that clarity of the formulation is selected from the group consisting of clear, substantially clear, translucent, slightly cloudy, and slightly hazy.

In another embodiment there is provided a process for preparing a formulation for anaesthetic use, comprising the step of dissolving propofol in a solvent, wherein the solvent is selected from the group consisting of glycofurol, Solutol HS15, a polyglycol ester of polyethylene glycol and 12-hydroxystearic acid, and mixtures thereof.

According to a seventh aspect of the invention, there is provided a process for preparing a formulation for anaesthetic use, comprising the steps of:

solubilising propofol in a solvent; and diluting the solution in water, wherein said solvent is clinically acceptable and wherein the formulation does not contain a condensation product of ethylene oxide with a fatty acid, or with a vegetable oil, or with a long chain aliphatic alcohol, or with a partial ester derived from a fatty acid and a hexitol anhydride, or with propylene oxide, and wherein the amounts of solvent and water in the formulation are such that the propofol is solubilised therein. The solvent may be a polyglycol ester of polyethylene glycol and 12-hydroxystearic acid.

In an embodiment, the ratio of the solvent to water is such that the clarity of the formulation is selected from the group consisting of clear, substantially clear, translucent, transparent, slightly cloudy, and slightly hazy. This may be between 1:10 and 2:5, and preferably may be about 1:5.

The process may additionally comprise dissolving other components such as are desirable in the formulation, for example antimicrobial agents. Said dissolving other components may be performed either before or after diluting in water.

In another embodiment there is provided a process for preparing a formulation for anaesthetic use, comprising the steps of:

solubilising propofol in a solvent; and diluting the solution in water, wherein said solvent is selected from the group consisting of glycofurol, Solutol HS15, a polyglycol ester of polyethylene glycol and 12-hydroxystearic acid and mixtures thereof.

According to an eighth aspect of the invention, there is provided a process for preparing a formulation for anaesthetic use, comprising the steps of:

dissolving propofol in a first solvent;
adding a second solvent; and
performing one or more of shaking, stirring, and allowing the mixture to stand, sufficient to render the mixture substantially homogeneous.

In this process, the first and second solvents are clinically acceptable, the first solvent is not a condensation product of ethylene oxide with a fatty acid, or with a vegetable oil, or with a long chain aliphatic alcohol, or with a partial ester derived from a fatty acid and a hexitol anhydride, or with propylene oxide, and the second solvent is not ethanol or a glycol or a polyethylene glycol or a glycol monoether or a water soluble ester or amide, and the amounts of the first and second solvents in the formulation are such that the propofol is solubilised therein. The second solvent may be a polyglycol ester of polyethylene glycol and 12-hydroxystearic acid.

In an embodiment, the ratio of the first solvent to the second solvent is such that the clarity of the formulation is selected from the group consisting of clear, substantially clear, translucent, slightly cloudy, and slightly hazy, and may be between 6-1 and 0.6:1, or between 4:1 and 1:1, or between 3:1 and 1:1, or may be about 2:1. In this specification, the term "substantially clear" should be taken as including substantially clear, transparent, transparent without being cloudy, and transparent but slightly hazy.

In another embodiment, there is provided a process for preparing a formulation for anaesthetic use, comprising the steps of:

dissolving propofol in a first solvent;
adding a second solvent; and performing one or more of shaking, stirring and allowing the mixture to stand, sufficient to render the mixture substantially homogeneous;

wherein the first solvent is selected from the group consisting of glycofurol, Macrogol 400, polyethylene glycol (PEG), propylene glycol and mixtures thereof and the second solvent is Solutol HS15, a polyglycol ester of polyethylene glycol and 12-hydroxystearic acid, or a mixture thereof, or the first solvent is glycofurol and the second solvent is selected from the group consisting of all esters of long-chain polyethylene glycol with structures containing no less than 10 carbon atoms.

With reference to the sixth, seventh and eighth aspects, other components may be added to the formulation after addition of the solvent, or of the first solvent or of the second solvent, or they may be combined with the solvent, or with the first solvent or with the second solvent before said solvent is mixed with propofol. Alternatively, said other components may be combined with propofol before a solvent is added. Said or other materials that are of benefit in the formulation.

According to a ninth aspect of the present invention there is provided a process of preparing a formulation for anaesthetic use comprising the steps of:

mixing the propofol with a first solvent and a second solvent, wherein the first solvent is not a condensation product of ethylene oxide with a fatty acid, or with a vegetable oil, or with a long chain aliphatic alcohol, or with a partial ester derived from a fatty acid and a hexitol anhydride, or with propylene oxide, and the second solvent is not ethanol or a glycol or a polyethylene glycol or a glycol monoether or a water soluble ester or amide, and diluting with water, wherein the amounts of the first and second solvents in the formulation are such that the propofol is solubilised.

The water may be added portionwise or as a single addition. The second solvent may be a polyglycol ester of polyethylene glycol and 12-hydroxystearic acid.

In an embodiment, propofol is mixed with the first solvent and thereafter the mixed propofol and first solvent is mixed with the second solvent. In an alternative embodiment, propofol is mixed with the second solvent and thereafter the mixed propofol and second solvent is mixed with the first solvent. In another alternative embodiment, propofol is mixed at the same time with the first and second solvents.

In another embodiment there is provided a process of preparing a formulation for anaesthetic use comprising the steps of:

mixing the propofol with a first solvent and a second solvent, and diluting with water, wherein the first solvent is selected from the group consisting of glycofurol, Macrogol 400, polyethylene glycol (PEG), propylene glycol and mixtures thereof and the second solvent is Solutol HS15, a polyglycol ester of polyethylene glycol and 12-hydroxystearic acid, or a mixture thereof, or the first solvent is glycofurol and the second solvent is selected from the group consisting of all esters of long-chain polyethylene glycol with structures containing no less than 10 carbon atoms, and wherein the amounts of the first and second solvents in the formulation are such that the clarity of the formulation is selected from the group consisting of clear, substantially clear, translucent, slightly cloudy, and slightly hazy.

In the ninth aspect, propofol may be in the range of about 0.5% to about 1.5%; the first solvent may be in the range of about 5% to about 40%; the second solvent which is different from said first solvent may be in the range of about 5% to about 15%; and the amount of water may be up to 100%.

The compositions made by the process of the invention may be capable of infinite dilution with water without phase separation.

The process of the invention may include the step of adding one or more clinically acceptable auxiliary agents in a total amount of up to 10%. The auxiliary agents may be added to the propofol, first solvent and second solvent mixture, and, in the case where there are more than one such auxiliary agents, they may be added at the same time or they may be added at different times. The auxiliary agents may be a viscosity-modifying agent, an antimicrobial preservative and/or an antioxidant and/or other suitable auxiliary agent(s). The auxiliary agent(s) is/are used in non toxic amount(s) in the formulations of the invention.

Clinically acceptable means pharmaceutically acceptable or veterinarially acceptable.

It will be understood by those skilled in the art that the exact order of the above process steps need not be followed as detailed but that the order may be varied with alternative and/or additional steps added.

The formulation may be filled into ampoules, vials or other suitable containers and terminally sterilised by moist heat in an autoclave or it may be aseptically filled into said ampoules, vials or other suitable containers.

According to a tenth aspect of the invention there is provided a formulation when made by the process of the sixth, seventh eighth or ninth aspects of the invention.

According to an eleventh aspect of the invention there is provided an admixture of the formulation of first, second, third, fourth, fifth or tenth aspects of the invention and a solution selected from Ringers Solution, Hartmanns Solution, Dextrose Solution, Saline Solution and Sterile Water for Injection.

According to a twelfth aspect of the invention there is provided a method of inducing and/or maintaining anaesthesia or sedation in a vertebrate, comprising administering to said vertebrate an effective amount of a formulation according to the first, second, third, fourth, fifth or tenth aspects of the invention, or of an admixture according to the eleventh aspect.

According to a thirteenth aspect of the invention; there is provided a formulation of the first, second, third, fourth, fifth or tenth aspects of the invention, or an admixture according to the eleventh aspect, when used to induce and/or maintain anaesthesia or sedation in a vertebrate.

The vertebrate may be a mammal, a marsupial or a reptile. The mammal may be a primate or non-human primate or other non-human mammal. The mammal may be selected from the group consisting of human, non-human primate, equine, murine, bovine, leporine, ovine, caprine, feline and canine. The mammal may be selected from a human, horse, cattle, sheep, dog, cat, goat, llama, rabbit and a camel, for example.

DETAILED DESCRIPTION OF THE INVENTION

In a particular form, the present invention is directed to an aqueous anaesthetic formulation comprising propofol and a first solvent, a second solvent which is different from said first solvent, and water, wherein the first solvent is not a condensation product of ethylene oxide with a fatty acid, or with a vegetable oil, or with a long chain aliphatic alcohol, or with a partial ester derived from a fatty acid and a hexitol anhydride, or with propylene oxide, and the second solvent is not ethanol or a glycol or a polyethylene glycol or a glycol monoether or a water soluble ester or amide, and amounts of said first solvent and said second solvent are clinically acceptable. The formulation may be or is capable of infinite dilution with water without phase separation.

The first solvent may be selected from the group consisting of glycofurol, Macrogol 400, polyethylene glycol (PEG), and propylene glycol or a mixture thereof and the second solvent may be Solutol HS15 (polyethylene glycol 660 12-hydroxy stearate). Alternatively, the first solvent may be glycofurol and the second solvent may be selected from the group consisting of all esters of long-chain polyethylene glycol with structures containing no less than 10 carbon atoms or a polyglycol ester of polyethylene glycol and 12-hydroxystearic acid.

Suitably, the formulation of the invention may be clear, substantially clear, translucent, translucent without being cloudy, transparent, transparent without being cloudy, slightly hazy or transparent but slightly hazy. Preferably, the formulation according to the invention is not cloudy, turbid or opaque.

Suitably, the combined amount of the first solvent and second solvent in the formulation is clinically acceptable and as a result presents minimal or no risk of anaphylactoid reactions in susceptible patients.

Suitably, formulations according to the invention are capable of infinite dilution with water without phase separation. Suitably, propofol remains solubilised upon infinite dilution with water or other therapeutically acceptable fluids. Suitably, propofol does not precipitate when the formulation is diluted with an aqueous diluent. Suitably, when diluted with water or another therapeutically acceptable fluid, the visual appearance of the formulation remains substantially clear or slightly translucent, and does not become cloudy, turbid or opaque. Alternatively the formulation may become cloudy during the dilution process but become clear, substantially clear, translucent, translucent without being cloudy, transparent, transparent without being cloudy, slightly hazy or transparent but slightly hazy on continued addition of water.

As an example of a preferred solvent system suitable for use in the present invention, the first solvent is glycofurol and the second solvent is Solutol HS15. Without being bound by any particular mechanism of action of the solvent system, it is thought that glycofurol exerts its solubilization action by an inter-molecular bonding effect between the glycofurol, propofol and water. On the other hand the Solutol HS15 is thought to solubilize the propofol by encapsulation of the drug in micelles of the compound. This proposed mechanism of action reduces the free concentration of propofol in the aqueous phase and may be critical in the incidence of pain at the injection site on administration of the formulation. It is believed that the incidence of pain at the injection site is related to the concentration of the free propofol in the aqueous phase.

The solvent system used in the present formulation allows for reduced toxic potential as a result of the lowered total dose of the individual solvents. In addition, the present solvent system not only solubilises the propofol in an aqueous formulation but also allows the propofol to remain solubilised on subsequent dilution with commonly used intravenous solutions.

The formulation of the present invention has been developed to confer several advantages over currently available propofol formulations and formulations described in the prior art. For instance, the formulation of the present invention contains no lipid, eg phosphatide, thereby avoiding complications associated with administration over prolonged periods of time, or to patients with disorders of fat metabolism.

A further advantage of the formulation according to the present invention is that it can be mixed with a variety of commonly used infusion fluids including Ringers Solution, Hartmanns Solution, Dextrose Solutions, Saline Solution, Sterile Water, at infinite dilution prior to administration, which is especially advantageous in various clinical applications.

In addition, a formulation according to the present invention is capable of being terminally sterilised by moist heat, eg autoclaving, which is particularly advantageous for enhanced sterility assurance of pharmaceuticals.

Optionally, the formulation may include at least one antimicrobial preservative that prevents microbial growth in the event of microbial contamination of the formulation. In addition, as the formulation does not include any lipid, it is of minimal nutritive value to microorganisms and therefore does not support rapid growth in the event of microbial contamination.

Suitably, the formulation passes the BP and/or USP antimicrobial preservative efficacy testing.

Optionally, the formulation of the invention may additionally include at least one antioxidant which may inhibit photochemical changes in the formulation over time. Suitable antioxidants include butylated hydroxyanisole, propyl gallate and butylated hydroxytoluene.

Suitably, the compositions of the invention may be placed in ampoules, vials or other suitable containers. Commonly, the containers are aseptically filled. Also, commonly, the pharmaceutical formulations of the invention are terminally sterilised using techniques known in the art, eg autoclaving.

Suitably, formulations according to the present invention are shelf stable following first use for periods of 6-12 months, typically 6 months. For example, chemical and microbial testing demonstrates formulations according to the present invention retain acceptable chemical and microbial characteristics up to and including 6 months after first broaching of the immediate packaging container such as multidose vial.

Formulations of the invention may be diluted with Water for Injections or introduced into other fluids suitable for either intravenous bolus injection or for intravenous infusion, including Ringers Solution, Hartmanns Solution, Dextrose Solutions, Saline Solution, Sterile Water The formulations may be diluted infinitely in a variety of physiological and non-physiological solutions and fluids without affecting the physical state of propofol or its biological activity.

The formulation may be administered as is, or after dilution in a suitable diluent, by intravenous bolus, slow intravenous injection or intravenous infusion, for the induction or maintenance of anaesthesia and sedation in animals, including humans.

The invention will now be described in greater detail by reference of specific Examples, which should not be construed as in any way limiting the scope of the invention.

EXAMPLE 1

A formulation comprising the following:

| Propofol | 1% w/v; |
| Glycofuranol | 10% w/v; |
| Solutol ® HS15 | 5% w/v; |
| Benzyl Alcohol | 2% w/v; |
| Ethanol | 2% w/v; |
| Water for Injections | to 100% w/v. |

The above formulation is prepared as follows:

Propofol is dissolved in the glycofuranol. Solutol® HS15 is added, the formulation is mixed and left to allow complete solubilization. Benzyl alcohol is added, with stirring. A portion of the Water for Injections is added, with stirring. Ethanol is added, with stirring. The remainder of the Water for Injections is added to volume, with stirring.

Visual appearance: lightly opaque

EXAMPLE 2

A formulation comprising the following:

| Propofol | 1% w/v |
| Glycofuranol | 10% w/v |
| Solutol HS15 | 10% w/v |
| Benzyl Alcohol | 2% w/v |
| Ethanol | 2% w/v |
| Water for Injections | to 100%. |

The above formulation is prepared as follows:

Solutol HS15 is added and melted by warming, glycofuranol is added, propofol is added and the formulation is mixed. Benzyl alcohol is added and mixed, and ethanol is added and mixed. Water for Injections is added to volume, with mixing.

Visual appearance: slightly opalescent

EXAMPLE 3

A formulation comprising the following:

| Propofol | 1% w/v |
| Glycofuranol | 20% w/v |
| Solutol HS 15 | 10% w/v |
| Benzyl Alcohol | 2% w/v |
| Ethanol | 2% w/v |
| Water for Injections | to 100%. |

The above formulation is prepared as follows:

Propofol is dissolved in the glycofuranol. Solutol HS15 is added, the formulation is mixed and left to allow complete solubilization. A portion of the Water for Injections is added, with stirring. Benzyl alcohol is added, with stirring. Ethanol is added, with stirring. The remainder of the Water For Injections is added to volume, with stirring.

Visual appearance: Clear solution

EXAMPLE 4

A formulation comprising the following:

| Propofol | 1% w/v |
| Glycofuranol | 20% w/v |
| Solutol HS 15 | 10% w/v |
| Benzyl Alcohol | 2% w/v |
| Ethanol | 2% w/v |
| Butylated hydroxytoluene | 0.02% |
| Water for Injections | to 100%. |

The above formulation is prepared as follows:

Propofol is dissolved in the glycofuranol. Solutol HS15 is added, the formulation is mixed and left to allow complete solubilization. A portion of the Water for Injections is added, with stirring. Benzyl alcohol is added, with stirring. Butylated hydroxytoluene is added to the ethanol and mixed, and the solution is added to the formulation. The remainder of the Water for Injections is added to volume, with stirring.

Visual appearance: Clear solution

EXAMPLE 5

A formulation comprising the following:

| Propofol | 1% w/v |
| Glycofuranol | 20% w/v |
| Solutol HS15 | 10% w/v |
| Benzethonium Chloride | 0.02% w/v |
| Ethanol | 2% w/v |
| Water for Injections | to 100%. |

The above formulation is prepared as follows:

Solutol HS15 is added and melted by warming, glycofuranol is added, propofol is added and the formulation is mixed. Ethanol is added and mixed. Water for Injections is added, with mixing and benzethonium chloride is added and mixed.

Visual appearance: Substantially clear solution

EXAMPLE 6

A formulation comprising the following:

| Propofol | 1% w/v |
| Glycofuranal | 20% w/v |
| Solutol HS 15 | 10% w/v |
| Benzalkonium Chloride | 0.02% w/v |
| Ethanol | 2% w/v |
| Water for Injections | to 100%. |

The above formulation is prepared as follows:

Solutol HS15 is added and melted by warming, glycofuranol is added, propofol is added and the formulation is mixed. Ethanol is added and mixed. Water for Injections is added, with mixing and benzalkonium chloride is added and mixed.

Visual appearance: Substantially clear solution

EXAMPLE 7

A formulation comprising the following:

| Propofol | 1% w/v |
| Macrogol 400 | 20% w/v |
| Solutol HS 15 | 10% w/v |
| Benzyl Alcohol | 2% w/v |
| Ethanol | 2% w/v |
| Water for Injections | to 100%. |

The above formulation is prepared as follows:

Solutol HS15 is added and melted by warming, Macrogol 400 is added and mixed, propofol is added and the formulation is mixed. Benzyl alcohol is added and mixed. Ethanol is added and mixed. Water for Injections is added, with mixing.

Visual appearance: Lightly translucent, whitish bloom

EXAMPLE 8

A formulation comprising the following:

| Propofol | 1% w/v |
| Propylene Glycol | 20% w/v |
| Solutol HS 15 | 10% w/v |
| Benzyl Alcohol | 2% w/v |
| Ethanol | 2% w/v |
| Water for injections | to 100%. |

The above formulation is prepared as follows:

Solutol HS15 is added and melted by warming, propylene glycol is added and mixed, propofol is added and the formulation is mixed. Benzyl alcohol is added and mixed. Ethanol is added and mixed. Water for Injections is added, with mixing.

Visual appearance: Substantially clear solution

EXAMPLE 9

A formulation comprising the following:

| Propofol | 1% w/v |
| Solutol HS15 | 20% w/v |
| Benzyl Alcohol | 2% w/v |
| Ethanol | 2% w/v |
| Water for Injections | to 100%. |

The above formulation is prepared as follows:

Solutol HS15 is added and melted by warming, mixed, propofol is added and the formulation is mixed. Benzyl alcohol is added and mixed. Ethanol is added and mixed. Water for Injections is added, with mixing.

Visual appearance: Substantially clear, slightly yellow solution.

EXAMPLE 10

The formulation of Example 3 was subjected to simulated in-use testing for a period of 6 months. As indicated in the table below, the formulation retains acceptable chemical and microbial properties as follows:

| Attribute | Initial | 14 Days | 28 Days | 3 months | 6 months |
| --- | --- | --- | --- | --- | --- |
| pH | 4.71 | 4.58 | 4.49 | 4.41 | 4.14 |
| Propofol % Label claim | 102.5% | 101.4% | 101.5% | 99.7% | 98.3% |
| Benzyl Alcohol % Label claim | 99.5% | 98.7% | 100.7% | 102.1% | 98.2% |
| Sterility (BP/Ph Eur 1998) | Complies | Not tested | Complies | Not tested | Complies |
| Preservative Efficacy Testing (BP/USP) | Not tested | Not tested | Complies | Not tested | Complies |

EXAMPLE 11

The formulation of Example 3 was subjected to in vivo trials in New Zealand White Rabbits to compare the pharmacokinetics and clinical effects of the formulation with that of the commercially available propofol formulation Diprivan (Astra Zeneca). Each rabbit was injected intravenously with either the trial formulation or Diprivan at a dose rate of propofol 5 mg/kg. Clinical effect was recorded and serial blood samples collected following injection. Blood samples were assayed by high performance liquid chromatography (HPLC) for propofol content.

Both groups behaved in a similar manner clinically. Pharmacokinetic parameters were not significantly different and the two formulations were thereby considered to be bioequivalent under the conditions of the study. The example formulation of the invention did not significantly affect the pharmacological effect of propofol.

We claim:

1. A formulation for anesthetic use consisting of:
   propofol,
   a solvent,
   benzyl alcohol as an antimicrobial agent, and
   ethanol as a pharmaceutically acceptable viscosity-modifying agent,
   wherein the solvent is selected from the group consisting of glycofurol, Solutol HS15 (polyethylene glycol 660 hydroxy stearate), a polyglycol ester of polyethylene glycol and 12-hydroxystearic acid, and mixtures thereof, and wherein the ratio of propofol to the solvent is such that the propofol is solublised.

2. The formulation of claim 1 wherein the ratio of propofol to solvent is between 1:199 and 1:6.

3. The formulation of claim 1 wherein the ratio of propofol to solvent is between 1:30 and 1:8.

4. An admixture of a formulation according to claim 1 and a solution selected from Ringers Solution, Hartmanns Solution, Dextrose Solution, Saline Solution and Sterile Water for Injection.

5. A method of inducing and/or maintaining anaesthesia or sedation in a vertebrate, comprising administering to said vertebrate and effective amount of a formulation according to claim 1.

6. A formulation according to claim 1 said formulation being capable of infinite dilution with water without phase separation.

7. The formulation of claim 1 wherein the benzyl alcohol is present at between about 0.1 to 10% in the formulation.

8. The formulation of claim 1 wherein the benzyl alcohol is present at about 2% in the formulation.

9. The formulation of claim 1 wherein the ethanol is present at between about 0.5 and 5% in the formulation.

10. A formulation for anesthetic use consisting of:
    propofol,
    a solvent,
    benzyl alcohol as an antimicrobial agent,
    ethanol as a pharmaceutically acceptable viscosity-modifying agent, and
    water,
    wherein the solvent is selected from the group consisting of glycofurol, Solutol HS15 (polyethylene glycol 660 hydroxy stearate), a polyglycol ester of polyethylene glycol and 12-hydroxystearic acid, and mixtures thereof, and wherein the amounts of solvent and water in the formulation is such that the propofol is solublised.

11. The formulation of claim 10 wherein the ratio of solvent to water is between 1:40 and 1:2.

12. The formulation of claim 10 wherein the ratio of solvent to water is between 1:10 and 3:10.

13. The formulation of claim 10 wherein the benzyl alcohol is present at between about 0.5 to 5% in the formulation.

14. The formulation of claim 10 wherein the ethanol is present at between about 0.5 and 5% in the formulation.

15. A formulation for anesthetic use consisting of:
    propofol,
    a first solvent, and
    a second solvent which is different to said first solvent,
    wherein the first solvent is selected from the group consisting of glycofurol, Macrogol 400 (polyethylene glycol 400), polyethylene glycol (PEG), propylene glycol and mixtures thereof and the second solvent is selected from the group consisting of Solutol HS15(polyethylene glycol 660 hydroxy stearate), a polyglycol ester of polyethylene glycol and 12-hydroxystearic acid, and mixtures thereof, and wherein the amounts of the first and second solvents in the formulation are such that the propofol is solublised.

16. The formulation of claim 15 wherein the ratio of the first solvent to the second solvent is between 6:1 and 0.6:1.

17. The formulation of claim 15 wherein the ratio of the first solvent to the second solvent is between 3:1 and 1:1.

18. An admixture of a formulation according to claim 15 and a solution selected from Ringers Solution, Hartmanns Solution, Dextrose Solution, Saline Solution and Sterile Water for Injection.

19. A method of inducing and/or maintaining anaesthesia or sedation in a vertebrate, comprising administering to said vertebrate are effective amount of a formulation according to claim 15.

20. A formulation for anesthetic use consisting of:
    propofol,
    a first solvent,
    a second solvent which is different from said first solvent, and
    water,
    wherein the first solvent is selected from the group consisting of glycofurol, Macrogol 400 (polyethylene glycol 400), polyethylene glycol (PEG), propylene glycol and mixtures thereof and the second solvent is Solutol HS15(polyethylene glycol 660 hydroxy stearate), a polyglycol ester of polyethylene glycol and 12-hydroxystearic acid, or a mixture thereof and wherein the amounts of propofol, the first and second solvents and water in the formulation are such that the propofol is solublised, and wherein the formulation is made by combining a solution of propofol in the first solvent and the second solvent and combining said solution with water.

21. A formulation for anesthetic use consisting of:
    propofol in a range of about 0.5% to about 1.5%,
    a first solvent in a range of about 10% to about 30%;
    a second solvent which is different from said first solvent in a range of about 5% to about 15% ; and
    water to 100%,
    wherein the formulation contains no fats, the first solvent is glycofurol and the second solvent is Solutol HS15(polyethylene glycol 660 hydroxy stearate) and the concentrations of glycofurol and Solutol HS15(polyethylene glycol 660 hydroxy stearate) in the formulation are such that the risk of causing anaphylactoid reactions in susceptible individuals is low or negligible, and wherein the formulation is made by combining a solution of propofol in the first solvent and the second solvent and combining said solution with water.

22. A formulation for anaesthetic use consisting of:

| | |
|---|---|
| Propofol | 1% w/v |
| Glycofuranol | 20% w/v |
| Solutol HS 15 (polyethylene glycol 660 hydroxy stearate) | 10% w/v |
| Benzyl Alcohol | 2% w/v |
| Ethanol | 2% w/v |
| Water for Injections | to 100%. |

23. A formulation according to claim 22 which is a clear solution.

24. A formulation for anaesthetic use consisting of:
propofol,
a first solvent,
a second solvent which is different to said first solvent,
benzyl alcohol as an antimicrobial agent, and
ethanol as a pharmaceutically acceptable viscosity-modifying agent,
wherein the first solvent is selected from the group consisting of glycofurol, Macrogol 400 (polyethylene glycol 400), polyethylene glycol (PEG), propylene glycol and mixtures thereof and the second solvent is selected from the group consisting of Solutol HS15(polyethylene glycol 660 hydroxy stearate), a polyglycol ester of polyethylene glycol and 12-hydroxystearic acid, and mixtures thereof, and wherein the amounts of the first and second solvents in the formulation are such that the propofol is solublised.

25. A formulation for anaesthetic use consisting of:
propofol,
a first solvent,
a second solvent which is different from said first solvent, and
benzyl alcohol as an antimicrobial agent,
ethanol as a pharmaceutically acceptable viscosity-modifying agent, and
water,
wherein the first solvent is selected from the group consisting of glycofurol, Macrogol 400 (polyethylene glycol 400), polyethylene glycol (PEG), propylene glycol and mixtures thereof and the second solvent Solutol HS15 (polyethylene glycol 660 hydroxy stearate), a polyglycol ester of polyethylene glycol and 12-hydroxystearic acid, and mixtures thereof and wherein the amounts propofol, the first and second solvents and water in the formulation are such that the propofol is solublised.

26. A formulation for anaesthetic use consisting of:
propofol in a range of about 0.5% to about 1.5%;
a first solvent in a range of about 10% to about 30%;
a second solvent which is different from said first solvent in a range of about 5% to about 15%;
benzyl alcohol as an antimicrobial agent,
ethanol as a pharmaceutically acceptable viscosity-modifying agent, and
water to 100%,
wherein the formulation contains no fats, the first solvent is glycofurol and the second solvent is Solutol HS15 (polyethylene glycol 660 hydroxy stearate) and the concentrations of glycofurol and Solutol HS15 (polyethylene glycol 660 hydroxy stearate) in the formulation are such that the risk of causing anaphylactoid reactions in susceptible individuals is low or negligible.

27. The formulation of claim 26 wherein the benzyl alcohol is present at between about 0.5 to 5% in the formulation.

28. The formulation of claim 26 wherein the ethanol is present at between about 0.5 and 5% in the formulation.

29. A formulation for anaesthetic use consisting of:
propofol, and
a solvent,
wherein the solvent is selected from the group consisting of glycofurol, Solutol HS15 (polyethylene glycol 660 hydroxy stearate), a polyglycol ester of polyethylene glycol and 12-hydroxystearic acid, and mixtures thereof, and wherein the ratio of propofol to the solvent is such that the propofol is solubilised.

30. A formulation for anaesthetic use consisting of:
propofol,
a solvent, and
water,
wherein the solvent is selected from the group consisting of glycofurol, Solutol HS15 (polyethylene glycol 660 hydroxy stearate), a polyglycol ester of polyethylene glycol and 12-hydroxystearic acid, and mixtures thereof, and wherein the amounts of solvent and water in the formulation is such that the propofol is solubilised.

31. A formulation for anaesthetic use by intravenous administration consisting of:
propofol, and
a solvent,
wherein the solvent is selected from the group consisting of glycofurol, Solutol HS15 (polyethylene glycol 660 hydroxy stearate), a polyglycol ester of polyethylene glycol and 12-hydroxystearic acid, and mixtures thereof, and wherein the ratio of propofol to the solvent is such that the propofol is solubilised.

32. A formulation for anaesthetic use by intravenous administration consisting of:
propofol,
a solvent, and
water,
wherein the solvent is selected from the group consisting of glycofurol, Solutol HS15 (polyethylene glycol 660 hydroxy stearate), a polyglycol ester of polyethylene glycol and 12-hydroxystearic acid, and mixtures thereof, and wherein the amounts of solvent and water in the formulation is such that the propofol is solubilised.

33. A formulation for anaesthetic use by intravenous administration consisting of:
propofol,
a first solvent, and
a second solvent which is different to said first solvent,
wherein the first solvent is selected from the group consisting of glycofurol, Macrogol 400 (polyethylene glycol 400), polyethylene glycol (PEG), propylene glycol and mixtures thereof and the second solvent is selected from the group consisting of Solutol HS15 (polyethylene glycol 660 hydroxy stearate), a polyglycol ester of polyethylene glycol and 12-hydroxystearic acid, and mixtures thereof, and wherein the amounts of the first and second solvents in the formulation are such that the propofol is solubilised and wherein said formulation does not contain a condensation product of ethylene oxide with propylene oxide.

* * * * *